US010260085B2

(12) United States Patent
Horn et al.

(10) Patent No.: US 10,260,085 B2
(45) Date of Patent: Apr. 16, 2019

(54) DETECTING THE DECOMPOSITION OF ENZYMES IN A TEST ELEMENT BY MEANS OF CONTROLLED RELEASE OF A PROTECTED ANALYTE

(75) Inventors: Carina Horn, Biblis (DE); Dieter Heindl, Paehl (DE); Hans-Peter Haar, Wiesloch (DE); Nelli Steinke, Lampertheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 282 days.

(21) Appl. No.: 13/524,199

(22) Filed: Jun. 15, 2012

(65) Prior Publication Data

US 2013/0052674 A1 Feb. 28, 2013

Related U.S. Application Data

(63) Continuation of application No. PCT/EP2010/069760, filed on Dec. 15, 2010.

(30) Foreign Application Priority Data

Dec. 16, 2009 (EP) .................................... 09179500

(51) Int. Cl.
C12Q 1/54 (2006.01)

(52) U.S. Cl.
CPC ..................... *C12Q 1/54* (2013.01)

(58) Field of Classification Search
CPC ............ G01N 27/127; G01N 33/0031; G01N 33/0057; C12N 9/0006; C12N 9/96; C12Q 1/54

See application file for complete search history.

(56) References Cited

U.S. PATENT DOCUMENTS

| 4,066,403 | A | * | 1/1978 | Bruschi | ........................... | 435/12 |
| 4,649,121 | A | | 3/1987 | Ismail et al. | | |
| 5,801,006 | A | | 9/1998 | Kaufman | | |
| 7,517,467 | B2 | * | 4/2009 | Shin et al. | ...................... | 216/65 |
| 7,548,773 | B2 | | 6/2009 | Noble | | |
| 7,553,615 | B2 | * | 6/2009 | Heindl et al. | ..................... | 435/4 |
| 2003/0211006 | A1 | * | 11/2003 | Qian et al. | ........................ | 422/56 |
| 2004/0126831 | A1 | * | 7/2004 | Van Antwerp | .................. | 435/14 |
| 2007/0196899 | A1 | | 8/2007 | Goto et al. | | |
| 2009/0123955 | A1 | | 5/2009 | Marfurt | | |
| 2011/0281287 | A1 | * | 11/2011 | Marfurt | ........................... | 435/11 |
| 2013/0011871 | A1 | * | 1/2013 | Horn et al. | ..................... | 435/26 |

FOREIGN PATENT DOCUMENTS

| CA | 2721718 A1 * | 8/2009 |
| CN | 101058824 A | 10/2007 |
| CN | 101329264 A | 12/2008 |
| CN | 101329268 A | 12/2008 |
| DE | 29620452 U1 | 11/1996 |
| EP | 0 217 246 A3 | 9/1986 |
| EP | 1 739 432 B1 | 6/2005 |
| EP | 1 965 198 A1 | 2/2007 |
| EP | 1965198 A1 * | 9/2008 |
| WO | WO 98/33936 | 8/1998 |
| WO | WO 01/49247 A3 | 7/2001 |
| WO | WO 2005/045016 A2 | 5/2005 |
| WO | WO 2005/084530 A2 | 9/2005 |
| WO | WO 2006/065900 A1 | 6/2006 |
| WO | WO 2007/012494 A1 | 2/2007 |
| WO | WO 2007127981 A2 * | 11/2007 |
| WO | WO 2009103540 A1 * | 8/2009 |
| WO | WO 2011/073258 A1 | 6/2011 |

OTHER PUBLICATIONS

Deng et al. (2008) Biosensors and Bioelectronics 24(4): 957-63.*
PCT/EP2010/069760; IPRP; dated Apr. 3, 2012.
Extended European Search Report dated Apr. 16, 2010 (English translation attached).
Tusa, J.K./Leiner, M.J.P., Florescent Optical Sensors for Critical Care Analytes, Symposium International, May 30-31, 2002.
Sang-Ho Baik et al., Cooperative Effect of Two Surface Amino Acid Mutations (Q252L and E170K) in Glucose Dehydrogenase from Bacillus megaterium IWG3 on Stabilization of Its Oligomeric State, Applied and Environmental Microbilogy, Jun. 2005, pp. 3285-3293, vol. 71 No. 6, Copyright 2005 American Society of Microbiology.
Edward J. Hutchinson et al., Synthesis of Carbocyclic NAD+ Containing a Methylenebisphosphonate Linkage for the Investigation of ADP-ribosyl Cyclase, Chem. Commun., 1996, pp. 2765-2766.
Eduardo Vazquez-Figueroa et al., Development of a Thermostable Glucose Dehydrogenase by a Structure-Guided Consensus Concept, ChemBioChem, 2007, pp. 2295-2301, 8, Copyright 2007 Wiley-VCH Verlag GmbH & Co. KGaA, Weinheim.
James T. Slama et al., Inhibition of NAD Glycohydrolase and ADP-ribosyl Transferases by Carbocyclic Analogues of Oxidized Nicotinamide Adenine Dinucleotide, Biochemistry, 1989, pp. 7688-7694, 28, Copyright 1989 American Chemical Society.
James T. Slama et al., Carbanicotinamide Adenine Dinucleotide: Synthesis and Enzymological Properties of a Carbocyclic Analogue of Oxidized Nicotinamide Adenine Dinucleotide, Biochemistry, 1988, pp. 183-193, 27, Copyright 1988 American Chemical Society.
International Search Report, dated Feb. 8, 2011, Roche Diagnostics Corporation.
Brauchle, Christoph, Spectral Hole Burning at Room Temperature and with a Single Molecule: Two New Perspectives, Agnew. Chem. Int. Ed. Engl. 31 (1992) No. 4, pp. 426-429.
Joachim Hones et al., The Technology Behind Glucose Meters: Test Strips, Diabetes Technology & Therapeutics, 2008, pp. S10-S26, vol. 10, Supplement 1, Copyright Mary Ann Liebert, Inc.

* cited by examiner

*Primary Examiner* — Lisa J Hobbs
(74) *Attorney, Agent, or Firm* — Roche Diabetes Care, Inc.

(57) ABSTRACT

In one form, a diagnostic element for determining at least one analyte is provided. In a further form, an analytical measuring device includes the diagnostic element. Still, other forms are related to methods for the determination of an analyte, correcting a signal generated by an analyte, and/or checking the detection optics of an analytical measuring device using the diagnostic element. Another form is related to a system for the controlled release of a reagent and the use of such a system as a circuit element. Other aspects include, but are not limited to, unique methods, techniques, products, systems and devices involving diagnostic elements.

19 Claims, 6 Drawing Sheets

Specification includes a Sequence Listing.

5A

5B

6A

6B

7A small bright spot in the light-blue layer
= burnt-off material

GlucDH_E96G_E170K (SEQ ID NO 1)

M Y P D L K G K V V A I T G A A S G L G K A M A I R F G K E
Q A K V V I N Y Y S N K Q D P N E V K E E V I K A G G E A V
V V Q G D V T K E E D V K N I V Q T A I K E F G T L D I M I
N N A G L G N P V P S H E M P L K D W D K V I G T N L T G A
F L G S R E A I K Y F V E N D I K G N V I N M S S V H E V I
P W P L F V H Y A A S K G G I K L M T K T L A L E Y A P K G
I R V N N I G P G A I N T P I N A E K F A D P K Q K A D V E
S M I P M G Y I G E P E E I A A V A V W L A S K E S S Y V T
G I T L F A D G G M T K Y P S F Q A G R G

GlucDH_E170K_K252L (SEQ ID NO 2)

M Y P D L K G K V V A I T G A A S G L G K A M A I R F G K E
Q A K V V I N Y Y S N K Q D P N E V K E E V I K A G G E A V
V V Q G D V T K E E D V K N I V Q T A I K E F G T L D I M I
N N A G L E N P V P S H E M P L K D W D K V I G T N L T G A
F L G S R E A I K Y F V E N D I K G N V I N M S S V H E V I
P W P L F V H Y A A S K G G I K L M T K T L A L E Y A P K G
I R V N N I G P G A I N T P I N A E K F A D P K Q K A D V E
S M I P M G Y I G E P E E I A V A V W L A S K E S S Y V T
G I T L F A D G G M T L Y P S F Q A G R G

DETECTING THE DECOMPOSITION OF ENZYMES IN A TEST ELEMENT BY MEANS OF CONTROLLED RELEASE OF A PROTECTED ANALYTE

CROSS-REFERENCE TO RELATED APPLICATIONS

This application is a continuation of International Application No. PCT/EP2010/069760 filed Dec. 15, 2010, which claims priority to European Patent Application No. 09179500.5 filed Dec. 16, 2009. Each of the referenced applications is incorporated herein by reference in its entirety.

FIELD OF THE INVENTION

The present application concerns a diagnostic element as well as a process for its production.

BACKGROUND

Diagnostic elements are important components of clinically relevant analytical methods. This primarily concerns the measurement of analytes such as metabolites or substrates which are determined directly or indirectly for example with the aid of a specific enzyme for the analyte. In this case, the analytes are converted with the aid of an enzyme-coenzyme complex and subsequently quantified. In this process, the analyte to be determined is contacted with a suitable enzyme, a coenzyme and optionally a mediator where the coenzyme is physicochemically changed by the enzymatic reaction. For example, the coenzyme may be oxidized or reduced by the enzymatic reaction. If a mediator is used, it typically transfers the electrons released from the reduced coenzyme during the conversion of the analyte onto an optical indicator or the conductive components of an electrode so that the process can be detected photometrically or electrochemically. A calibration yields a direct relationship between the measured value and the concentration of the analyte to be determined.

Diagnostic elements known from the prior art are characterized by a limited shelf-life and by special requirements, such as cooling or dryness, for the environment in which they are stored in order to achieve this shelf-life. With certain types of application, for example in the case of tests that are carried out by the end user himself such as blood glucose self monitoring, erroneous results that can hardly be detected by the user may therefore occur due to a false unnoticed incorrect storage of the measuring system and may lead to improper treatment of the respective disease.

The erroneous results are primarily based on the fact that the enzymes, coenzymes and/or mediators used in such diagnostic elements may generally react sensitively to moisture and heat and, as a result, are inactivated in whole or in part. Thus, when glucose is detected by means of a glucose dehydrogenase/NAD system under warm and humid environmental conditions for example, the activity of the glucose dehydrogenase enzyme as well as the content of the NAD coenzyme decrease over time and the decrease in the coenzyme generally proceeds considerably more rapidly than the loss of activity of the enzyme.

A known measure that is used to increase the stability of diagnostic elements is to use stable enzymes, such as those enzymes from thermophilic organisms. Furthermore, it is possible to stabilize enzymes by chemical modification such as cross-linking, or by mutagenesis. Moreover, enzyme stabilizers such as trehalose, polyvinyl pyrrolidone and serum albumin for example can be added or the enzymes can be enclosed in polymer networks by, for example, photopolymerization.

Another method for improving the stability of diagnostic elements is to use stabilized coenzymes. Whereas native coenzymes such as NAD and NADP or their reduced forms NADH and NADPH for example are relatively unstable under basic or acidic conditions due to the lability of the glycosyl bond between the ribose and the pyridine unit, various derivatives of NAD/NADH and NADP/NADPH have been described in the literature in recent years which significantly increase the stability of the coenzyme by modification of the nicotinamide group or the ribose unit.

The stability of diagnostic elements can also be increased by using stable mediators. Thus, the specificity of tests is increased and interferences during the reaction are eliminated by using mediators having a redox potential that is as low as possible. However, the redox potentials of the enzyme/coenzyme complexes form a lower limit for the redox potential of mediators. If the potential is lower than this limit, the reaction with the mediators is slowed down or even stopped.

However, the components of chemical detection reagents that are used in diagnostic elements do not all have the same stability in practice, but rather are subject to decomposition processes that occur at different rates. Thus, when carbaNAD is used as a coenzyme for example, the effect occurs that the coenzyme remains very stable over a long period even under humid conditions and at elevated temperatures due to the carbacyclic sugar unit, whereas the activity of a native enzyme used in the diagnostic element continuously decreases. Likewise, if a combination of a stabilized enzyme and a native coenzyme is used for example, the activity of the enzyme can be maintained over a long period whereas the amount of coenzyme rapidly decreases to a greater or lesser extent due to thermal and/or hydrolytic decomposition.

In order to avoid erroneous results when determining analytes, diagnostic elements should allow a determination of whether the individual components of a detection reagent used in the diagnostic element are still in a functional form at the time of measurement and that the detection reagent is inasmuch suitable for the qualitative and/or quantitative detection of the analyte. In this connection, the determination of the enzyme activity is particularly problematic because the inactivation of an enzyme is firstly caused by a change in the conformation of the protein and hence no optically-active or electrochemically-active particles are formed because there is no change in the constitution.

In view of the foregoing, one non-limiting object of the present application is to provide a stable diagnostic element for determining an analyte such as glucose in which the disadvantages of the prior art are at least partially eliminated. In one aspect, the diagnostic element should ensure that in the case of a greatly reduced or completely absent functionality of individual components of a detection reagent, one avoids showing measurement results that are allegedly correct with respect to a particular analyte.

In one non-limiting aspect, the above-identified object is achieved by a diagnostic element for determining at least one analyte that includes a detection reagent that is specific for the analyte and an indicator analyte having a defined amount of the at least one analyte. The indicator analyte is present in a releasable form that is inaccessible for a reaction with the detection reagent.

SUMMARY

In one form, a diagnostic element for determining at least one analyte is provided. In a further form, an analytical measuring device includes the diagnostic element. Still, other forms are related to methods for the determination of an analyte, correcting a signal generated by an analyte, and/or checking the detection optics of an analytical measuring device using the diagnostic element. Another form is related to a system for the controlled release of a reagent and the use of such a system as a circuit element. Other aspects include, but are not limited to, unique methods, techniques, products, systems and devices involving diagnostic elements.

In one embodiment, a diagnostic element for determining at least one analyte includes a detection reagent that is specific for the analyte. The diagnostic element also includes an indicator analyte having a defined amount of the at least one analyte. The indicator analyte is present in a releasable form that is inaccessible for a reaction with the detection reagent.

In another embodiment, an analytical measuring device includes a diagnostic element for determining at least one analyte and that includes a detection reagent that is specific for the analyte. The diagnostic element also includes an indicator analyte having a defined amount of the at least one analyte. The indicator analyte is present in a releasable form that is inaccessible for a reaction with the detection reagent.

In a further embodiment, a method for determining an analyte includes contacting the analyte with a diagnostic element for determining at least one analyte and that includes a detection reagent that is specific for the analyte. The diagnostic element also includes an indicator analyte having a defined amount of the at least one analyte. The indicator analyte is present in a releasable form that is inaccessible for a reaction with the detection reagent. The method also includes determining at least one of analyte presence and an amount of the analyte.

In yet another embodiment, a method for correcting a signal generated by an analyte includes inserting a diagnostic element into an analytical measuring device. The diagnostic element is configured for determining at least one analyte and includes a detection reagent that is specific for the analyte. The diagnostic element also includes an indicator analyte having a defined amount of the at least one analyte. The indicator analyte is present in a releasable form that is inaccessible for a reaction with the detection reagent. The method also includes generating a first detectable signal in the analytical measuring device by contacting the analyte with the diagnostic element; generating a second detectable signal in the analytical measuring device by releasing the indicator analyte in the diagnostic element; and correcting the first signal using the second signal.

In still another embodiment, a method for checking detection optics of an analytical measuring device includes inserting a diagnostic element into the analytical measuring device. The diagnostic element is configured for determining at least one analyte and includes a detection reagent that is specific for the analyte. The diagnostic element also includes an indicator analyte having a defined amount of the at least one analyte. The indicator analyte is present in a releasable form that is inaccessible for a reaction with the detection reagent. The method also includes generating a detectable signal in the analytical measuring device by releasing the indicator analyte in the diagnostic element, and correlating the detectable signal with a reference signal.

Another embodiment is directed to a system for the controlled release of a reagent and that includes a carrier including the reagent and a separate reaction system. The reagent is present in a form that is inaccessible for a reaction with the reaction system under normal conditions and releasable for a reaction with the reaction system under defined conditions. The system also includes means for releasing the reagent on the carrier.

Other aspects include unique compositions, methods, techniques, systems and devices involving diagnostic elements.

Further embodiments, forms, objects, features, advantages, aspects, and benefits shall become apparent from the following description and drawings.

BRIEF DESCRIPTION OF THE DRAWINGS

FIG. 8 illustrates amino acid sequences of the glucose dehydrogenase double mutants GlucDH_E96G_E170K and GlucDH_E170K_K252L.

DETAILED DESCRIPTION

Figure 1:
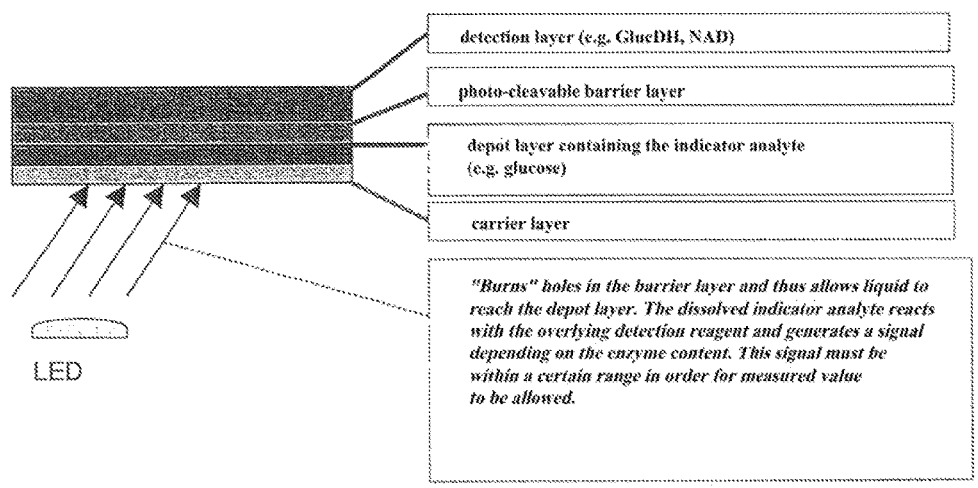
FIG. 1 is a cross-section view of one embodiment of a diagnostic element.

In one form, a diagnostic element for determining at least one analyte is provided. In a further form, an analytical measuring device includes the diagnostic element. Still, other forms are related to methods for the determination of an analyte, correcting a signal generated by an analyte, and/or checking the detection optics of an analytical measuring device using the diagnostic element. Another form is related to a system for the controlled release of a reagent and the use of such a system as a circuit element. Other aspects include, but are not limited to, unique methods, techniques, products, systems and devices involving diagnostic elements.

The detection reagent used in the diagnostic elements disclosed herein may be a chemical detection reagent and may include any components that are suitable for determining an analyte using, for example, optical or electrochemical means. Examples of such components are known to a person skilled in the art and include enzymes, coenzymes, mediators, optical indicators as well as auxiliary substances and/or additives, just to provide a few non-limiting possibilities.

In one particular embodiment, the detection reagent includes at least one enzyme and/or coenzyme which independently of one another can be of natural, semi-synthetic or synthetic origin and can be freely selected by a person skilled in the art depending on the diagnostic element requirements. In one aspect, the detection reagent includes a combination of at least one enzyme and at least one coenzyme where the enzyme has a high specificity for the analyte to be determined and thus reduces erroneous results when determining the analyte.

If the diagnostic elements disclosed herein include an enzyme, the enzyme may be a coenzyme-dependent enzyme. Examples of these enzymes include, amongst others, dehydrogenases, oxidases such as glucose oxidase (EC 1.1.3.4) or cholesterol oxidase (EC 1.1.3.6) for example, aminotransferases such as aspartate or alanine aminotransferase for example, 5'-nucleotidase, creatine kinase and diaphorase (EC 1.6.99.2).

In one more specific embodiment, a nicotinamide adenine dinucleotide (NAD/NADH)-dependent dehydrogenase or a nicotinamide adenine dinucleotide phosphate (NADP/NADPH)-dependent dehydrogenase is used as the enzyme. In more particular forms of this embodiment, the enzyme is selected in from the group of an alcohol dehydrogenase (EC 1.1.1.1; EC 1.1.1.2), an L-amino acid dehydrogenase (EC 1.4.1.5), a glucose dehydrogenase (EC 1.1.1.47), a glucose-6-phosphate dehydrogenase (EC 1.1.1.49), a glycerol dehydrogenase (EC 1.1.1.6), a 3-hydroxybutyrate dehydrogenase (EC 1.1.1.30), a lactate dehydrogenase (EC 1.1.1.27; 1.1.1.28), a malate dehydrogenase (EC 1.1.1.37) and a sorbitol dehydrogenase. In another more particular form, the enzyme is a glucose dehydrogenase (EC 1.1.1.47) or a glucose-6-phosphate dehydrogenase (EC 1.1.1.49).

If a glucose dehydrogenase (EC 1.1.1.47) is used as the enzyme, then it is possible for example to use a mutated glucose dehydrogenase. The term "mutant" as used within the scope of the present document refers to a genetically modified variant of a native enzyme which, while having the same number of amino acids, has a modified amino acid sequence compared to the wild-type enzyme; i.e., it differs from the wild-type enzyme by at least one amino acid. The introduction of the mutation(s) can take place site-specifically or non-site-specifically. In one form, the introduction takes place site-specifically using recombinant methods known in the specialized field which results in at least one amino acid substitution within the amino acid sequence of the native enzyme depending on the respective requirements and conditions. In one aspect, the mutant has an increased thermal or hydrolytic stability compared to the wild-type enzyme. Examples of such mutants are described by Baik (Appl. Environ. Microbiol. (2005), 71, 3285), Vásquez-Figueroa (Chem. Bio. Chem. (2007), 8, 2295) as well as in International Patent Publication No. WO 2005/045016 A2, the disclosure of which is hereby incorporated herein by reference in its entirety.

The mutated glucose dehydrogenase can have the amino acid(s) that is/are modified compared to the corresponding wild-type glucose dehydrogenase basically at any position in its amino acid sequence. In one form, the mutated glucose dehydrogenase includes a mutation at at least one of the positions 96, 170 and 252 of the amino acid sequence of the wild-type glucose dehydrogenase In particular form, the mutated glucose dehydrogenase includes at position 96 and position 170 or mutations at position 170 and position 252. It has proven to be advantageous when the mutated glucose dehydrogenase contains no further mutations apart from these mutations.

The mutations at positions 96, 170 and 252 can in principle comprise any amino acid substitution which leads to a stabilization, such as an increase of the thermal or hydrolytic stability, of the wild-type enzyme. In one form, the mutation at position 96 includes an amino acid substitution of glutamic acid by glycine whereas with reference to position 170 an amino acid substitution of glutamic acid by arginine or lysine. In one particular form, the amino acid substitution at position 170 includes the substitution of glutamic acid by lysine. With regard to the mutation at position 252, it may include an amino acid substitution of lysine by leucine.

The mutated glucose dehydrogenase can be obtained by mutation of a wild-type glucose dehydrogenase derived from any biological source, where the term "biological source" in the sense of this document encompasses prokaryotes such as bacteria for example, as well as eukaryotes such as mammals and other animals for example. In one form, the wild-type glucose dehydrogenase is derived from a bacterium such as *Bacillus megaterium, Bacillus subtilis* or *Bacillus thuringiensis*.

In one particular embodiment, the mutated glucose dehydrogenase is a glucose dehydrogenase obtained by mutating wild-type glucose dehydrogenase from *Bacillus subtilis* which has the amino acid sequence shown in SEQ ID NO:1 (GlucDH_E96G_E170K) or the amino acid sequence shown in SEQ ID NO: 2 (GlucDH_E170K_K252L).

In one embodiment, the diagnostic elements described herein may include a coenzyme which may be a stabilized coenzyme. A stabilized coenzyme within the sense of the present document is a coenzyme that has been chemically modified compared to the native coenzyme, and which compared to the native enzyme has a higher stability at atmospheric pressure towards moisture, temperatures, particularly in the range of 0° C. to 50° C., acids and bases, particularly in the range of pH 4 to pH 10, and/or nucleophiles, such as alcohols and amines for example. Similarly, stabilized coenzymes can be active over a longer period than the native coenzyme under identical environmental conditions.

In one form, the stabilized coenzyme has a higher hydrolytic stability compared to the native coenzyme, and may for example have a complete stability towards hydrolysis under typical test conditions. The stabilized coenzyme may also have a reduced or increased binding constant for the enzyme compared to the native coenzyme. For example, in one aspect the binding constant may be reduced or increased by a factor of two or more.

Non-limiting examples of stabilized coenzymes include stabilized NAD(P)/NAD(P)H compounds; i.e., chemical derivatives of native nicotinamide adenine dinucleotide (NAD/NADH) and nicotinamide adenine dinucleotide phosphate (NADP/NADPH) or the compound of formula (I):

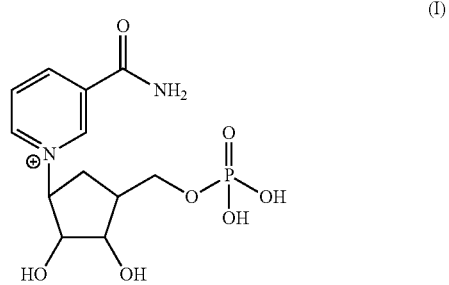 [SMILES: NC(=O)c1ccc[n+](C2CC(COP(=O)(O)O)C(O)C2O)c1]

If the stabilized coenzyme is a stabilized NAD(P)/NAD(P)H compound, the stabilized NAD(P)/NAD(P)H compound may include a 3-pyridine carbonyl residue or a 3-pyridine thiocarbonyl residue which is linked without a glycosidic bond to a phosphorus-containing residue, such as a phosphate residue for example, by a linear or cyclic organic residue. In one particular form, the residue is a cyclic organic residue.

In one form, the stabilized NAD(P)/NAD(P)H compound is selected from compounds of the general formula (II):

(II)

in which
A=adenine or an analogue thereof;
T=in each case independently denotes O or S;
U=in each case independently denotes OH, SH, $BH_3^-$ or $BCNH_2^-$;
V=in each case independently denotes OH or a phosphate group, or two groups that form a cyclic phosphate group;
W=COOR, $CON(R)_2$, COR, or $CSN(R)_2$ where R=in each case independently denotes H or a $C_1$-$C_2$ alkyl;
$X^1$, $X^2$=in each case independently denote O, $CH_2$, $CHCH_3$, $C(CH_3)_2$, NH, or $NCH_3$;
Y=NH, S, O, or $CH_2$;
Z=a linear or cyclic organic residue, provided that Z and the pyridine residue are not linked together by a glycosidic bond, or a salt or reduced form thereof.

In one embodiment, the compounds of the general formula (II) contain adenine or adenine analogues such as, for example, $C_8$-substituted and $N_6$-substituted adenine, deaza variants such as 7-deaza, aza variants such as 8-aza or combinations such as 7-deaza or 8-aza or carbocyclic analogues such as formycin where the 7-deaza variants can be substituted at the 7 position by halogen, $C_{1-6}$ alkinyl, $C_{1-6}$ alkenyl or $C_{1-6}$ alkyl.

In a further embodiment, the compounds of the general formula (II) contain adenosine analogues which contain, for example, 2-methoxydeoxyribose, 2'-fluorodeoxyribose, hexitol, altritol or polycyclic analogues such as bicyclo, LNA and tricyclo sugars instead of ribose.

In particular forms of the compounds of the general formula (II), (di) phosphate oxygens can also be replaced isotonically such as, for example, O⁻ by S⁻ or $BH_3^-$, O by NH, $NCH_3$ or $CH_2$, and =O by =S. In particular but non-limiting forms, W in the compounds of the general formula (II) is $CONH_2$ or $COCH_3$.

In certain forms of the compounds of the general formula (II), Z is a linear residue containing 4-6 C atoms, and in one particular form 4 C atoms, in which 1 or 2 C atoms are optionally replaced by one or more heteroatoms selected from O, S and N, or a residue comprising a cyclic group containing 5 or 6 C atoms which optionally contains a heteroatom selected from O, S and N as well as optionally one or more substituents, and a residue $CR^4_2$, where $CR^4_2$ is bound to the cyclic group and to $X^2$, where $R^4$ in each case independently denotes H, F, Cl, or $CH_3$.

In one particular form, Z is a saturated or unsaturated carbocyclic or heterocyclic five-membered ring, and more particularly but not exclusively is a compound of the general formula (III)

(III)

in which a single or double bond can be present between $R^{5'}$ and $R^{5''}$, and
$R^4$=in each case independently denotes H, F, Cl, or $CH_3$;
$R^5$=O or $CR^4_2$;
$R^{5'}$=O, S, NH, $NC_1$-$C_2$-alkyl, $CR^4_2$, CHOH, or $CHOCH_3$, and $R^{5''}$=$CR^4_2$, CHOH, or $CHOCH_3$ if a single bond is present between $R^{5'}$ and $R^{5''}$;
$R^{5'}$=$R^{5''}$=$CR^4$ if a double bond is present between $R^{5'}$ and $R^{5''}$;
and
$R^6$, $R^{6'}$=in each case independently denote CH or $CCH_3$.

In one form, $R^5$ is O or $CH_2$ in the groups of the general formula (III). Furthermore, in one form $R^{5'}$ is selected from $CH_2$, CHOH and NH. In a particular embodiment, $R^{5'}$ and $R^{5''}$ are in each case CHOH. In yet another particular embodiment, $R^{5'}$=NH and $R^{5''}$=$CH_2$. One specific embodiment includes a compound of formula (II) in which $R^4$=H, $R^5$=O or $CH_2$, $R^{5'}$=$R^{5''}$=CHOH and $R^6$=$R^{6'}$=CH.

In still another particular embodiment, the stabilized NAD(P)/NAD(P)H compound is carbaNAD (J. T. Slama, Biochemistry (1988), 27, 183 and Biochemistry (1989), 28, 7688) or carbaNADP. Other stable coenzymes which can be used in the chemical detection reagents described herein are disclosed in International Patent Publication Nos. WO 98/33936, WO 01/49247, WO 2007/012494, U.S. Pat. No. 5,801,006, U.S. patent application Ser. No. 11/460,366 and the publication to Blackburn et al. published in *Chemical Communications* (Chem. Comm. (1996), 2765). Each of the above references is hereby incorporated herein by reference in its entirety.

In a further embodiment, the detection reagent includes at least one additional component which facilitates the qualitative detection and/or quantitative determination of the analyte. Examples of such at least one additional component include, for example, a mediator and/or an optical indicator. The term "mediator" as used within the scope of this document refers to a chemical compound which reacts with the reduced coenzyme that is obtained by reaction with the analyte, and enables electrons to be transferred to a suitable optical indicator or an optical indicator system or to electrochemical electrodes. Non-limiting examples of mediators include nitrosoanilines, such as [(4-nitrosophenyl)imino] dimethanol hydrochloride for example, quinines, such as phenanthrene quinones, phenanthroline quinones or benzo [h]-quinoline quinones for example, phenazines, such as 1-(3-carboxypropoxy)-5-ethyl-phenazinium trifluoromethane sulfonate for example, and/or diaphorase (EC 1.6.99.2).

Non-limiting examples of phenanthroline quinones include 1,10-phenanthroline-5,6-quinones, 1,7-phenanthroline-5,6-quinones, 4,7-phenanthroline-5,6-quinones as well as N-alkylated or N,N'-dialkylated salts thereof, wherein in the case of N-alkylated or N,N'-dialkylated salts halogenides, trifluoromethane sulfonate or other anions that increase the solubility may be used as counterions. Diaphorases that are particularly suitable for the purposes disclosed herein include, for example, diaphorase from pig heart, *Clostridium kluyverii* and *Bacillus stearothermophilus* as well as the diaphorase mutant described in U.S. Patent Publication No. 2007/0196899 A1 which has an improved catalytic function and thermostability compared to native diaphorases. The contents of this reference are hereby incorporated herein by reference in their entirety.

Any substance which is reducible and when reduced undergoes a detectable change in its optical properties can be used as an optical indicator. Non-limiting examples of such optical properties include colour, fluorescence, remission, transmission, polarization and/or refractive index. The determination of the presence and/or the amount of analyte in the sample can be carried out with the naked eye and/or by using an optical or electrochemical method which appears suitable to a person skilled in the art. Examples of optical methods include photometric and fluorimetric methods.

Heteropoly acids such as 2,18-phosphomolybdic acid for example which are reduced to the corresponding heteropoly blue are preferably used as optical indicators. Furthermore, it is also possible to use quinones such as, for example, resazurin, dichlorophenol indophenol and/or tetrazolium salts as optical indicators. Non-limiting examples of suitable tetrazolium include the products WST-3, WST-4 and WST-5 all commercially available from Dojindo Molecular Technologies, Inc., Kumamoto, Japan.

The diagnostic elements described herein additionally contain an indicator analyte having a defined amount of the at least one analyte to be determined which serves to generate a defined, optically or electrochemically detectable signal. If the magnitude of the signal generated by reaction of the indicator analyte with the detection reagent corresponds to a predetermined signal (reference signal) which correlates with an adequate amount of the individual components of the detection reagent present in a functional form that is required to determine the analyte (e.g. with an adequate amount of active enzyme), then the result of the actual measurement of the sample analyte may be released.

The term "in a functional form" as used herein means that the relevant component of the detection reagent is present in a chemically active form and can fulfil its intended function in the diagnostic element. In contrast, the term "in a non-functional form" means that the component is present in a chemically inactive form or does not fulfil its intended function despite being present in a chemically active form that differs from the form required to carry out the desired function.

The diagnostic elements described herein can be any test element which includes a dry reagent layer containing the detection reagent and can be wetted by a sample containing the analyte. In one form, the test elements disclosed herein include a carrier layer and a detection layer containing the detection reagent. In this case, the carrier layer can be made of any material onto which the detection layer can be applied using suitable techniques and which subsequently acts as a carrier for the detection reagent used to determine the analyte. The detection reagent can, in addition to an enzyme, coenzyme, mediator and/or optical indicator, optionally include further reagents that appear suitable to a person skilled in the art for the purposes of the respective application and/or are usually required to produce diagnostic elements such as, for example, auxiliary substances and/or additives.

The spatial positioning of the indicator analyte within the diagnostic elements disclosed herein includes various variants which can be selected by a person skilled in the art depending on the respective requirements and desired form. In one embodiment, the test elements described herein contain the indicator analyte in the detection layer such that the detection reagent and the indicator analyte are present in a common layer. In another embodiment, the indicator analyte is, in contrast, located in a depot layer that is separate from the detection layer. In one aspect, the depot layer is situated between the carrier layer and the detection layer where the depot layer is in direct contact with the detection layer or can be separated from this layer by one or more additional layers. In one form, a dissolvable barrier layer that can be dissolved photochemically or electrochemically for example, is in direct contact with the detection layer and may be arranged between a depot layer and the detection layer.

In order to avoid an uncontrolled reaction with the detection reagent of the diagnostic element and thus a falsification of the actual analyte measurement, the test elements disclosed herein contain the indicator analyte in a releasable form that is inaccessible for a reaction with the detection reagent. The term "in a releasable form that is inaccessible for reaction with the detection reagent" as used herein is to be regarded as being synonymous with the term "in a protected form" and encompasses any method of specifically preventing a (premature) reaction between the indicator analyte and the detection reagent. Measures for protecting the indicator analyte against an undesired chemical reaction include, among others, a chemical derivatization of the indicator analyte using suitable protecting groups, an encapsulation of the indicator analyte in a dissolvable matrix that is inert towards the detection reagent, and a spatial separation of the indicator analyte from the detection layer containing the detection reagent and/or the depot layer.

While the indicator analyte can be in direct contact with the detection reagent of the diagnostic element in the case of a chemical derivatization due to the inactivation that this causes, direct contact of the indicator analyte with the detection reagent must be avoided when using an indicator analyte that is not provided with chemical protecting groups. For this purpose, the indicator analyte can be, for example, encapsulated in an organic or inorganic matrix that is inert towards the detection reagent and which is dissolvable under defined conditions and releases the indicator analyte. Alternatively, in order to avoid a premature reaction with the detection reagent, the indicator analyte can be separated from the detection layer by a barrier layer which can be dissolved under at least one of the conditions defined below which enables the indicator analyte to be released from the depot layer into the detection layer for example.

In order to enable a chemical reaction with the detection reagent, the indicator analyte in the diagnostic element must be released at a given time from its form that is inaccessible for a reaction with the detection reagent. The release can take place using any suitable means, including for example photochemically by irradiation with light of a suitable wavelength or electrochemically by applying a voltage, and at any time, including before or after reaction of the detection reagent with the sample analyte in the process of which a protecting group of the indicator analyte that may be present is cleaved, a matrix containing the indicator analyte is at least partially dissolved, and/or a dissolvable barrier layer located between the depot layer and the detection layer is at least partially destroyed. The partial or complete destruction of the dissolvable matrix or barrier layer can, for example, take place using the method of spectral hole burning which can be used on crystalline and amorphous solid bodies and is used in particular in optical information processing, molecular electronics, integrated optics and optoelectronics (C. Bräuchle, "Angewandte Chemie" (1992), 104(4), 431-435).

In one aspect, polymer matrices containing energy absorbers are suitable for use for release methods utilizing spectral hole burning. The energy absorbers absorb energy depending on their absorption spectrum and release this energy into their local environment provided no other ways for energy reduction such as fluorescence radiation are available. Depending on the duration and intensity of the irradiation, the surrounding polymer matrix expands due to the heating effect, melts, bursts and/or undergoes chemical modification reactions. In this respect, a polymer matrix including at least one energy absorber can be used to encapsulate the indicator analyte and/or as a barrier layer which protects the indicator analyte from an undesired reaction with the detection reagent of the diagnostic element.

In the case of destroying or generating holes in the polymer matrix by irradiation with light of a suitable wavelength, in particular a wavelength that differs by at least 50 nm from the wavelength of the analyte measurement, it is possible to bring the indicator analyte into contact with the detection reagent under defined conditions and at any chosen time to generate a signal that can be measured optically or electrochemically for example. If the measurement of the analyte for example takes place in the ultraviolet range (i.e. at a wavelength in the range below 400 nm), in particular at a wavelength in the range from about 150 nm to about 400 nm, it is then possible for example to irradiate light at a wavelength of >400 nm, in particular light at a wavelength in the range of about 450 nm to about 800 nm in order to excite the energy absorber.

In view of the foregoing, the method described above generally enables systems to be provided for the controlled release of reagents in which the release can take place independently of other reaction processes in the system and thus allows a targeted control of reaction processes in the system. Consequently, a system which includes a carrier including a reagent that is present in a protected form and can be released under defined conditions and a reaction system that is separate therefrom, and means for releasing the reagent on the carrier, can be used for example as a circuit element in particular, but not exclusively, in the context of reaction cascades. In this connection, the reagent can be protected before reaction with the reaction system especially by encapsulation of the reagent in a dissolvable matrix, by spatial separation of the reagent from the reaction system by means of a dissolvable barrier layer, and/or by using chemical protecting groups as described in detail herein.

In one embodiment, the detection layer, the barrier layer and/or the depot layer of the test elements disclosed herein include a polymer matrix which contains at least one energy absorber as a result of which the indicator analyte can be protected from direct contact with the detection reagent before irradiating the diagnostic elements with light of a suitable wavelength as defined above. In one particular form, the polymer matrix containing the energy absorber can be embedded in the detection layer of the diagnostic elements described herein, or may be in the form of a separate layer designed as a barrier layer for example. In one form, the thickness of such a barrier layer is in the range of 0.05 µm to 5 µm. In a more particular form, the thickness of such a barrier layer is in the range of 1 µm to 3 µm. If the polymer matrix does not act as a barrier layer for the purposes of spatially separating an indicator analyte which has no chemical protecting groups from the detection layer for example, then the polymer matrix may also contain the indicator analyte in addition to the energy absorber. In one particular aspect of this form, the indicator analyte is encapsulated in the polymer matrix.

The polymer matrix may consist of at least one hydrophobic polymer which prevents the indicator analyte from showing signs of partial dissolution if the diagnostic element is contacted with moisture. More particularly, the polymer may be a hydrophobic organic polymer which promotes thermal hole formation and is stable at temperatures of 5° C. to 50° C.; i.e., it does not exhibit any signs of decomposition. In principle, any hydrophobic polymer that cannot be dissolved in or by water comes into consideration as the polymer which is suitable for forming a polymer matrix for the purposes disclosed herein. In one form, the polymer matrix described above is formed from a hydrophobic polymer selected from the group consisting of a polymethyl methacrylate (PMMA), a polyethyl methacrylate (PEMA), a polycarbonate and chemical derivatives thereof, although the use of other hydrophobic polymers known to a person skilled in the art is also contemplated.

It should be understood that the polymer matrix can contain the at least one energy absorber in different forms. For example, the at least one energy absorber may be covalently bound and/or present in a free form. In one particular form, the at least one energy absorber is covalently bound within the polymer matrix. If the polymer matrix contains a covalently bound energy absorber, then the energy absorber may be a direct component of the hydrophobic polymer. In one aspect, the energy absorber is integrated into the polymer chain of the hydrophobic polymer which can be accomplished by polymerizing suitable monomers of the energy absorber for example. In this manner, it is possible to ensure that a large number of molecules of the energy absorber is present in the polymer matrix that is obtained irrespective of the solubility of the selected energy absorber in a polymer solution used to produce the polymer matrix, which enables a high energy absorption and thus favours a dissolution of the polymer matrix for the purposes of releasing the indicator analyte. If, in contrast, the energy absorber should be present in the polymer matrix in a free form or unbound, i.e., if a polymer matrix doped with the energy absorber is to be generated, then this can be accomplished by simply mixing suitable polymer precursors and energy absorbers and subsequently polymerizing the mixture for example.

Depending on the respective requirements, it is possible to use an energy absorber as an energy absorber contained within the polymeric polymer matrix which at least partially releases the energy absorbed by irradiation to its local environment and thus results in a change in the polymer matrix. In order to facilitate hole formation, the polymer matrix and/or the hydrophobic polymer can, apart from the at least one energy absorber, additionally include thermally unstable compounds or thermally unstable functional groups which release highly volatile compounds such as nitrogen, carbon dioxide or other compounds that are gaseous at room temperature under appropriate heat application for example. Examples of such compounds or functional groups include azo derivatives, carbonic acid derivatives and cyclic alkenes, but are not limited to these.

In one particular form, the energy absorber is a hydrophobic dye which is highly soluble in the polymer matrix and/or emits no or only small amounts of fluorescence radiation after excitation and thus has a low quantum efficiency. In one particular form, the quantum efficiency is zero. Hydrophobic dyes may also be used which exhibit no or only a low absorption at the wavelength of the actual analyte measurement (for example at $\lambda=375$ nm), but have high extinction coefficients at orthogonal wavelengths (for example at $\lambda>500$ nm) which avoids the risk of an undesired release of the indicator analyte during the actual measurement. In this connection, cyanine dyes such as cryptocyanine, indotricarbocyanine (C7), oxacarbocyanine (C3), pinacyanol iodide, thiacarbocyanine (C3), thiadicarbocyanine (C5) or squarylium dyes such as squarylium dye III have proven to be particularly suitable.

In a further variant, the indicator analyte that is present in a releasable form that is inaccessible for a reaction with the detection reagent includes a photochemically and/or electrochemically cleavable protecting group which can be cleaved as required and in the process of which enables the indicator analyte to be released under defined conditions. Non-limiting examples of photochemically cleavable protecting groups which can be used to derivatize glucose include anthroquinone derivatives, benzoic acid derivatives, coumarin derivatives, nitrobenzophenone derivatives, thioxanthene derivatives, thioxanthenone derivatives, xanthene derivatives and veratryl derivatives, but are not limited to these. Non-limiting examples of electrochemically cleavable protecting groups which can be used within the scope of the present application include, among others, anthrone derivatives. A comprehensive overview of protecting groups in organic synthesis may be found in T. W. Greene, "Protecting Groups in Organic Synthesis", 2nd Edition, John Wiley and sons, New York, 1991.

As indicated above, the indicator analyte may be released before or after reaction of the detection reagent with the sample analyte. Whereas the detection reagent has not yet reacted with the analyte to be determined immediately (e.g. within the first second) after wetting the diagnostic element with the sample of the analyte and thus a reaction with the indicator analyte present in a defined amount can be monitored free from interference, about one second after wetting the diagnostic element one observes the onset of the conversion of the sample analyte dissolved in the sample. In this respect, a release of the indicator analyte in the diagnostic element is undesired from the onset of the conversion of the sample analyte until the time of almost complete conversion of the sample analyte because it is not usually possible to distinguish between the signals caused by the sample analyte and those caused by the indicator analyte. Hence, in one form the indicator analyte is not released until the sample analyte has been completely converted by the detection reagent and the generated signal is measured as part of a total system check.

The diagnostic elements disclosed herein can include a form onto which the analyte can be applied in the form of an aqueous or non-aqueous solution. In certain embodiments the diagnostic element is a test tape, test disk, test pad, a test strip, a test strip drum or the diagnostic elements mentioned in International Patent Publication No. WO 2005/084530 A2, the contents of which are hereby incorporated herein by reference in their entirety. In this connection, the diagnostic elements described in the present application each include at least one test area that can be brought into contact with a sample containing the analyte and enables a qualitative and/or quantitative determination of the analyte using any suitable means.

The term "test tape" as used herein refers to a tape-shaped diagnostic element which usually includes more than one individual test area, such as at least 10 individual test areas, at least 25 individual test areas or at least 50 individual test areas. The individual test areas may each be arranged at a distance of a few millimeters up to a few centimeters, for example at a distance of <2.5 cm from one another, and the test tape can optionally include marker areas between consecutive test areas to register the distance traveled during tape transport and/or for calibration. Such test tapes are described in European Patent Publication No. EP 1 739 432 A1, the contents of which are hereby incorporated herein by reference in their entirety.

The term "test disk" as used herein refers to a disk-shaped diagnostic element which can include one or more individual test areas, such as at least 10 individual test areas for example. In one embodiment, the test disk is coated with a thin layer of the test chemistry with a layer having a thickness of about 20 µm for example to which a sample of the analyte can be applied, wherein an area of the test disk of greater or lesser size is wetted by the sample depending on the volume of the sample and can be used to determine the analyte. The non-wetted area of the test disk which can be partially or completely wetted due to passage of moisture through the test chemistry layer is subsequently available for further determination of the analyte.

The diagnostic elements disclosed herein may be used to determine any biological or chemical substance that can be detected photochemically or electrochemically. In one form, the analyte is selected from the group consisting of malic acid, alcohol, ammonium, ascorbic acid, cholesterol, cysteine, glucose, glutathione, glycerol, urea, 3-hydroxybutyrate, lactic acid, 5'-nucleotidase, peptides, pyruvate, salicylate and triglycerides. In one particular form, the analyte is glucose. It should also be understood that the analyte can be derived from any source. In one aspect however, the analyte is present in a bodily fluid, non-limiting examples of which include whole blood, plasma, serum, lymph fluid, bile, cerebrospinal fluid, extracellular tissue fluid, urine and glandular secretions, such as saliva or sweat for example. In a further aspect, the diagnostic elements described herein are used to determine the presence and/or the amount of an analyte in a sample of whole blood, plasma, serum or extracellular tissue fluid.

In a further embodiment, the diagnostic elements described herein are designed for the determination of several analytes, where the term "several" as used herein denotes any number >1, including for example 2 to 10. In one form, the number of analytes is 2 to 5. In still another form, the number of analytes is 2 or 3. If it is intended to determine several analytes that can be present in a single or several different samples with the test elements described herein, then the different analytes can basically be determined in one and the same test area or in different test areas of a diagnostic element. For this purpose, the test elements disclosed herein can include for example a specific detection reagent and a defined amount of the respective analyte for each of the analytes to be determined. In one particular form, the diagnostic elements may be designed for the consecutive determination of the individual analytes by releasing the respective indicator analytes in the diagnostic element from different layers and/or at different times for example.

The qualitative and/or quantitative determination of the analyte can be carried out in any desired manner. For example, it is contemplated that all methods for detecting enzymatic reactions known in the art which generate a measurable signal that can be evaluated or read-out manually or using suitable means may be utilized. In one non-limiting form, optical detection methods which include, for example, the measurement of absorption, fluorescence, circular dichroism (CD), optical rotation dispersion (ORD), and/or refractometry are used. In another form, electrochemical detection techniques are used. In a further form, the analyte may be detected photometrically or fluorometrically indirectly by, for example, means of a fluorometrically detectable change of the coenzyme.

In another aspect, an analytical measuring device includes a diagnostic element described herein and enables the qualitative and/or quantitative determination of an analyte. Examples of such analytical measuring devices include, among others, the commercially available products ACCU-CHEK® ACTIVE, ACCU-CHEK® COMPACT and ACCU-CHEK® MOBILE analytical measuring devices (all from the Roche Company) but are not limited to these.

In yet a further aspect, a method for determining an analyte includes:

contacting the analyte with a diagnostic element disclosed herein; and determining the presence and/or the amount of the analyte.

In yet a further aspect, a method for correcting a signal generated by an analyte includes:

inserting a diagnostic element described herein into an analytical measuring device;

generating a first detectable signal in the analytical measuring device by contacting the analyte with the diagnostic element' generating a second detectable signal in the analytical measuring device by releasing the indicator analyte in the diagnostic element; and correcting the first signal using the second signal.

As part of the method described above, a diagnostic element disclosed herein is inserted into an analytical measuring device as described above for example. The analyte to be determined is then brought into contact with the diagnostic element, whereupon the analyte and the specific detection reagent for the analyte react with one another and a first optically or electrochemically detectable signal is generated in the analytical measuring device.

In order to evaluate to what extent the first measuring signal correctly represents the concentration of the analyte, the indicator analyte in the diagnostic element is released from its form in which it is inaccessible for a reaction with the detection reagent in a further step. The release may take place using methods as described in connection with the diagnostic elements disclosed herein. The indicator analyte released in this manner can then come into contact with the specific detection reagent for the analyte to generate a second optically or electrochemically detectable signal in the analytical measuring device which, due to the simultaneous detection of the analyte and released indicator analyte, is usually more pronounced than the first measuring signal.

By using suitable means such as a calibration curve for example, it is possible to relate the first and the second measuring signals which may be detected using two different measuring channels of a suitable analytical measuring device, in each case to a certain concentration of the analyte. If the concentration of the analyte calculated from the first measuring signal does not agree with the concentration of the analyte calculated from the second measuring signal, then the concentration of the analyte calculated from the first measuring signal is corrected using the result of the second measurement which can be carried out using a suitable algorithm for example. In this manner, it is possible to minimize potential variations of the measured value which may be due to environmental influences, such as temperature and/or air humidity, manufacturing-related irregularities in the diagnostic elements and/or the presence of interfering substances in the sample, and thus improve the accuracy of the analyte determination.

In yet a further aspect, a method for checking the detection optics of an analytical measuring device includes:

inserting a diagnostic element disclosed herein into the analytical measuring device;

generating a detectable signal in the analytical measuring device by releasing the indicator analyte in the diagnostic element; and correlating the detectable signal with a reference signal.

In particular one form, the method may be used to check for soiling of the detection optics of an analytical measuring device. After a diagnostic element disclosed herein has been inserted into the analytical measuring device and the indicator analyte has been released in the diagnostic element using methods that have been mentioned herein for example, a defined, optically or electrochemically detectable signal is generated in the analytical measuring device by reaction of the released indicator analyte with the specific detection reagent for the analyte and can be correlated with a reference signal.

If the detection optics of the analytical measuring device are soiled, a weaker signal is detected compared to the reference signal when the indicator analyte is reacted with the detection reagent, and the user can consequently be made aware of an impairment of the analytical measuring device by an optical or acoustic signal for example, and thereupon reject the measured value.

In yet a further aspect, a system for the controlled release of a reagent includes:

a carrier including the reagent and a separate reaction system, wherein the reagent is present in a releasable form that is inaccessible for a reaction with the reaction system under normal conditions and can be released for a reaction with the reaction system under defined conditions; and means for releasing the reagent on the carrier.

In yet a further aspect, a method includes using the release system described herein as a circuit element.

FIG. 1 illustrates a cross-section view of one embodiment of a diagnostic element that includes a detection layer, a photochemically cleavable barrier layer, a depot layer containing an indicator analyte, and a carrier layer.

Figure 2:
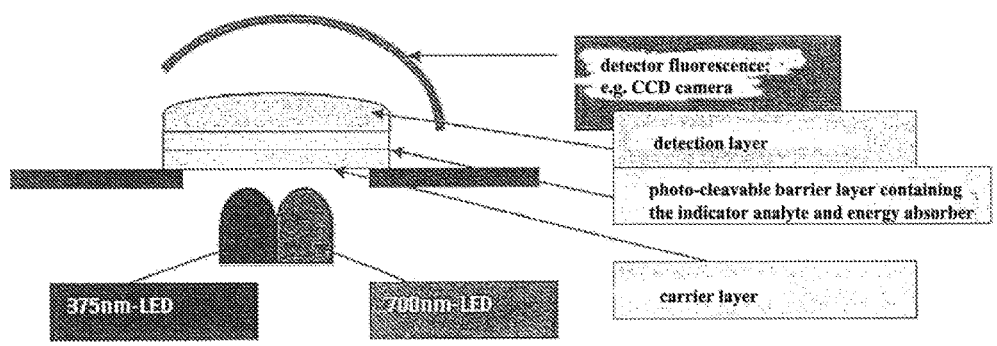
FIG. 2 is a cross-section view of an alternative embodiment of a diagnostic element.

FIG. 2 illustrates a cross-section of an alternative embodiment of a diagnostic element that includes a detection layer, a photochemically cleavable barrier layer containing an indicator analyte and energy absorber, and a carrier layer.

Figure 3:
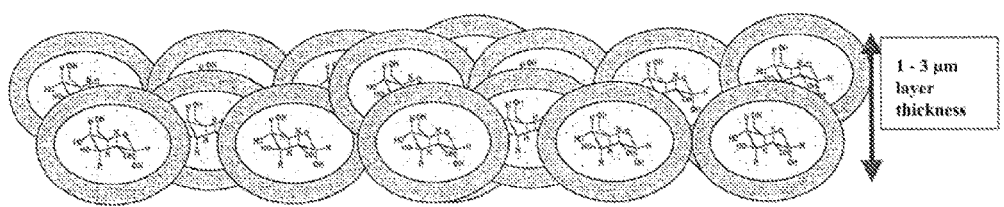
FIG. 3 is a cross-section view of a protection layer of a diagnostic element.

FIG. 3 illustrates a cross-section of the protection layer of a diagnostic element which contains the indicator analyte, in this case glucose, in an encapsulated form.

Figure 4:
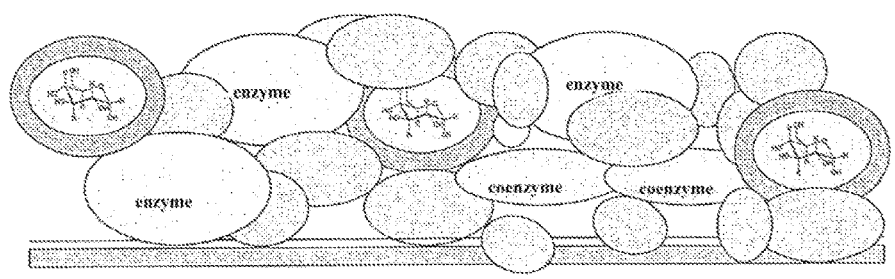
FIG. 4 is a cross-section view of a detection layer of a diagnostic element.

FIG. 4 illustrates a cross-section of the detection layer of a diagnostic element according to the invention which contains the indicator analyte (in this case glucose) in an encapsulated form.

Figure 5:
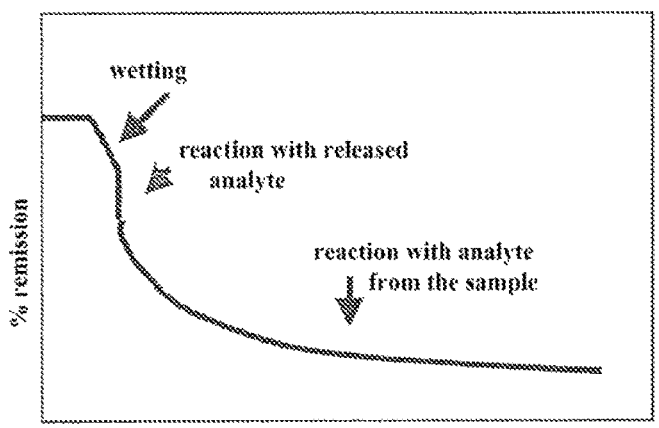
FIGS. 5A and 5B are graphical illustrations of conversion kinetics of an indicator analyte or sample analyte.
Figure 5:
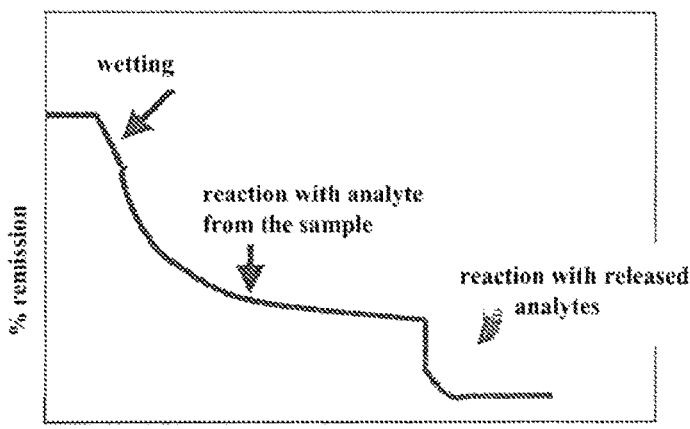

FIG. 5 is a graphical illustration of kinetics of the conversion of the indicator analyte or sample analyte by the enzyme system of a diagnostic element described herein. More particularly, FIG. 5A illustrates the release of the indicator analyte before the start of the conversion of the sample analyte by the enzyme system, and FIG. 5B illustrates the release of the indicator analyte after completion of the conversion of the sample analyte by the enzyme system.

Figure 6:
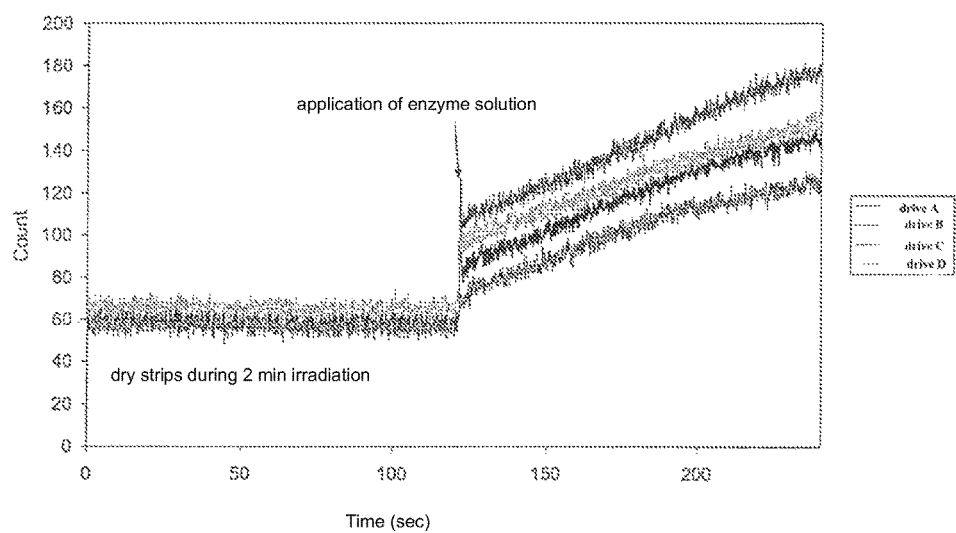
FIGS. 6A and 6B are graphical illustrations of fluorometric detection of an indicator analyte.
Figure 6:
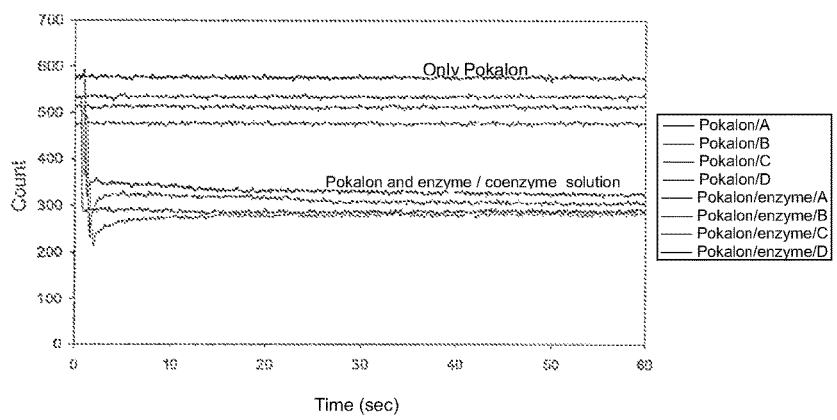

FIG. 6 is a graphical illustration of fluorometric detection of the indicator analyte by photochemical release and subsequent enzymatic reaction FIG. 6A graphically illustrates fluorescence of a diagnostic element irradiated with light of a suitable wavelength containing the indicator analyte in a derivatized form before and after contact with a solution of enzyme (GlucDH) and coenzyme (NAD). FIG. 6B graphically illustrates fluorescence of a diagnostic element that does not contain the indicator analyte in the absence or presence of a solution of enzyme (GlucDH) and coenzyme (NAD).

Figure 7:
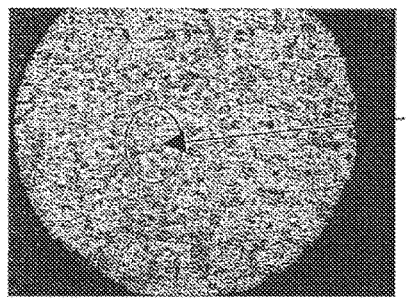
FIG. 7A-7C illustrate fluorometric detection of an indicator analyte by thermal hole formation and subsequent enzymatic reaction.
Figure 7:
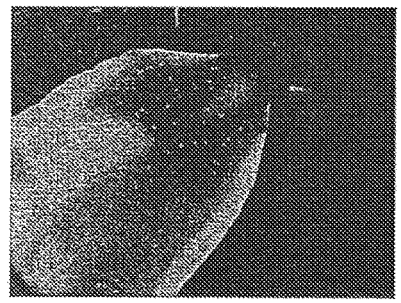
Figure 7:
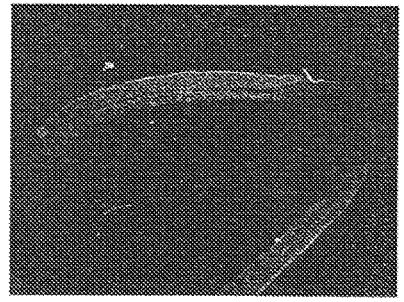

FIG. 7 illustrates fluorometric detection of the indicator analyte by thermal hole formation and subsequent enzymatic reaction. FIG. 7A provides a digital photograph of a polymer layer doped with dye (cryptocyanine) after 20 minutes irradiation with light of a suitable wavelength. FIG. 7B provides a digital photograph of a polymer layer doped with dye (cryptocyanine) after 20 minutes irradiation with light of a suitable wavelength and subsequent contact with a solution of enzyme (GlucDH) and coenzyme (NAD). FIG. 7C provides a digital photograph of a polymer layer doped with a dye (cryptocyanine) after contact with a solution of enzyme (GlucDH) and coenzyme (NAD) without previous irradiation.

FIG. 8 illustrates amino acid s of the glucose dehydrogenase double mutants GlucDH_E96G_E170K and GlucDH_E170K$_K$252L.

EXAMPLES

The following examples are for illustration purposes and are not to be construed as limiting the invention disclosed in this document to only the embodiments disclosed in these examples.

Example 1: Preparation and Use of a Diagnostic Element Containing an Indicator Analyte in a Derivatized Form Glucose in a derivatized form (Tris-veratryl derivative) and polyacrylamide (Aldrich Company) were applied together on a carrier layer of Pokalon foil (Lonza Company). The two-layered test element obtained in this manner was then placed on a luminescence measuring device (self-build Roche Company) and irradiated for two minutes with light of a wavelength of 375 nm. A solution of 10 mg glucose dehydrogenase (GlucDH, Roche Company) and 10 mg nicotinamide adenine dinucleotide (NAD; Roche Company) in 10 ml phosphate buffer, pH 7 (Merck Company) was then applied to the diagnostic element and the formation of NADH was monitored fluorometrically (see FIG. 6A) in order to detect the release of glucose from the glucose derivative used in the test element.

The empty Pokalon foil or the Pokalon foil in combination with the solution of GlucDH and NAD described above were each measured fluorometrically as a reference (see FIG. 6B).

Example 2: Preparation and Use of a Diagnostic Element Containing a Free Indicator Analyte and a Dye-Doped Polymer Matrix In order to prepare a diagnostic element containing a dye-doped polymer matrix, two Partial Solutions 1 and 2 were prepared which had the following compositions.

Partial Solution 1:

|  | Weighed amount (g) | Solids content (%) | Solid (g) | % on GFS |
|---|---|---|---|---|
| partial solution 1 | 100.00 | | | |
| PAA 1500 (polyacrylamide) | 60.00 | 50 | 30.00 | 33.33 |
| Glucose | 40.00 | 100 | 40.00 | 44.44 |

Partial Solution 2:

|  | Weighed amount (g) | Solids content (%) | Solid (g) | % on GFS |
|---|---|---|---|---|
| partial solution 2 | 4.41 | | | |
| 10% solution of PEMA in chloroform | 4.00 | 10 | 0.4 | 49.57 |
| cryptocyanine | 0.11 | 100 | 0.107 | 13.26 |
| Azo-bis(cyclohexyl) carbodiimide | 0.30 | 100 | 0.30 | 37.17 |

After preparation of the two Partial Solutions, a glucose-containing layer was produced from the Partial Solution 1 by coating with a doctor blade (30 µm wet layer thickness) and subsequently drying. The Partial Solution 2 was then coated (60 µm wet layer thickness) onto the dried layer containing the indicator analyte using a doctor blade and dried.

The dye-doped polymer layer obtained in this manner was irradiated with a hand-held laser (wavelength 650 nm, <5 watts) and after about 20 minutes holes could be observed in the irradiated layer (see FIG. 7A). A solution of 10 mg glucose dehydrogenase (GlucDH, Roche Company) and 10 mg nicotinamide adenine dinucleotide (NAD, Roche Company) in 10 ml phosphate buffer, pH 7 (Merck Company) was then applied to the holes generated by irradiation, whereupon the glucose released from the lower layer was oxidized by reaction with the enzyme system and greenish-blue fluorescent NADH was formed (see FIG. 7B).

As a reference, the above solution of glucose dehydrogenase (GlucDH) and nicotinamide adenine dinucleotide (NAD) in phosphate buffer, pH 7 was applied without prior irradiation of the dye-doped polymer layer onto the latter layer. In this case, due to the lack of thermally induced holes, no glucose is released from the lower layer and no NADH is formed (see FIG. 7C).

Although embodiments of the invention have been described using specific terms, such description is for illustrative purposes only, and it is to be understood that changes and variations obvious to the skilled artisan are to be considered within the scope of the claims that follow and their equivalents.

What is claimed is:

1. A diagnostic element for determining concentration or presence of at least one analyte in a body fluid sample, comprising:
   a carrier layer;
   a detection reagent that is specific for the at least one analyte, wherein the detection reagent comprises at least one of an enzyme and a coenzyme, wherein the detection reagent comprises at least one of a mediator and an optical indicator, wherein the detection reagent is part of a detection layer applied to the carrier layer;
   an indicator analyte, wherein the indicator analyte is a defined amount of the at least one analyte for generating a defined, optically or electrochemically detectable signal at a time that is distinct from any such signal generated by an amount of the analyte of interest detectable in the body fluid sample applied to the diagnostic element, wherein the indicator analyte is present in a releasable form that is physically inaccessible for a reaction with the detection reagent under normal conditions but that is releasable for a reaction with the detection reagent under defined conditions, wherein the indicator analyte is physically inaccessible for the reaction with the detection reagent under normal conditions by (1) being part of the detection layer but encapsulated in a polymer matrix comprising at least one energy absorber so that the polymer matrix is electrochemically or photochemically dissolvable, (2) being part of a depot layer that is applied between the carrier layer and the detection layer and separated from the detection layer by a barrier layer comprising the polymer matrix, or (3) being part of the detection layer but comprising an electrochemical or photochemical protecting group, and wherein the indicator analyte is encapsulated in an organic or inorganic matrix that is inert towards the detection reagent and which is dissolvable under defined conditions and releases the indicator analyte; and a configuration in the form of one a test tape, test disk, test pad and test strip drum.

2. The diagnostic element of claim 1, wherein the coenzyme is a stabilized coenzyme.

3. The diagnostic element of claim 1, wherein the reagent material comprises the enzyme and the enzyme is a nicotinamide adenine dinucleotide (NAD/NADH)-dependent or a nicotinamide adenine dinucleotide phosphate (NADP/NADPH)-dependent dehydrogenase.

4. The diagnostic element of claim 3, wherein the enzyme is a glucose dehydrogenase (EC 1.1.1.47) or a glucose-6-phosphate dehydrogenase (EC 1.1.1.49).

5. The diagnostic element of claim 3, wherein the reagent material further comprises the coenzyme and the coenzyme is a stabilized coenzyme selected from a stabilized nicotinamide adenine dinucleotide (NAD/NADH) compound and a stabilized nicotinamide adenine dinucleotide phosphate (NADP/NADPH) compound.

6. The diagnostic element of claim 5, wherein the stabilized coenzyme is selected from carbaNAD, carbaNADP, and a compound of formula (I)

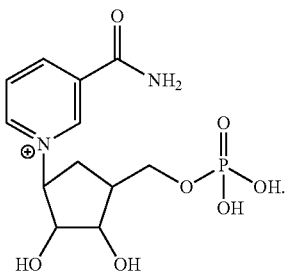

7. The diagnostic element of claim 1, wherein the reagent material comprises the coenzyme and the coenzyme is a stabilized coenzyme selected from a stabilized nicotinamide adenine dinucleotide (NAD/NADH) compound and a stabilized nicotinamide adenine dinucleotide phosphate (NADP/NADPH) compound.

8. The diagnostic element of claim 7, wherein the stabilized coenzyme is selected from carbaNAD, carbaNADP, and a compound of formula (I)

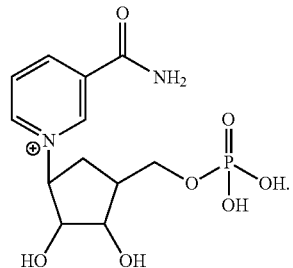

9. The diagnostic element of claim 1, wherein the polymer matrix is formed from at least one hydrophobic polymer.

10. The diagnostic element of claim 9, wherein the hydrophobic polymer is selected from the group consisting of a polymethyl methacrylate, a polyethyl methacrylate, a polycarbonate and chemical derivatives thereof.

11. The diagnostic element of claim 1, wherein the at least one energy absorber in the polymer matrix is at least one of covalently bound and in a free form.

12. The diagnostic element of claim 1, wherein the energy absorber is a hydrophobic dye selected from a cyanine dye, indotricarbocyanine (C7), oxacarbocyanine (C3), pinacyanol iodide, thiacarbocyanine (C3), thiadicarbocyanine (C5), and a squarylium dye.

13. The diagnostic element of claim 12, wherein the cyanine dye is cryptocyanine.

14. The diagnostic element of claim 12, wherein the squarylium dye is squarylium dye III.

15. The diagnostic element of claim 1, further comprising a configuration for the determination of several analytes.

16. An analytical measuring device, comprising a diagnostic element according to claim 1.

17. A method for determining an analyte, comprising:
contacting the analyte with a diagnostic element according to claim 1; and
determining at least one of analyte presence and an amount of the analyte.

18. The diagnostic element of claim 1, wherein the polymer is a hydrophobic organic polymer which promotes thermal hole formation and is stable at temperatures of about 5° C. to about 50° C.

19. The diagnostic element of claim 1, wherein the barrier has a thickness of about 0.05 μm to about 5 μm.

* * * * *

SEQUENCE LISTING

<160> NUMBER OF SEQ ID NOS: 2

<210> SEQ ID NO 1
<211> LENGTH: 261
<212> TYPE: PRT

```
<213> ORGANISM: Artificial
<220> FEATURE:
<223> OTHER INFORMATION: Mutant of glucose dehydrogenase from Bacillus
      subtilis
<220> FEATURE:
<221> NAME/KEY: MUTAGEN
<222> LOCATION: (96)..(96)
<220> FEATURE:
<221> NAME/KEY: MUTAGEN
<222> LOCATION: (170)..(170)

<400> SEQUENCE: 1

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Gln Gly
50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Gly
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
130                 135                 140

Ser Val His Glu Val Ile Pro Trp Pro Leu Phe Val His Tyr Ala Ala
145                 150                 155                 160

Ser Lys Gly Gly Ile Lys Leu Met Thr Lys Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Lys Ala Asp
        195                 200                 205

Val Glu Ser Met Ile Pro Met Gly Tyr Ile Gly Glu Pro Glu Glu Ile
210                 215                 220

Ala Ala Val Ala Val Trp Leu Ala Ser Lys Glu Ser Ser Tyr Val Thr
225                 230                 235                 240

Gly Ile Thr Leu Phe Ala Asp Gly Gly Met Thr Lys Tyr Pro Ser Phe
                245                 250                 255

Gln Ala Gly Arg Gly
            260

<210> SEQ ID NO 2
<211> LENGTH: 261
<212> TYPE: PRT
<213> ORGANISM: Artificial
<220> FEATURE:
<223> OTHER INFORMATION: Mutant of glucose dehydrogenase from Bacillus
      subtilis
<220> FEATURE:
<221> NAME/KEY: MUTAGEN
<222> LOCATION: (170)..(170)
<220> FEATURE:
<221> NAME/KEY: MUTAGEN
<222> LOCATION: (252)..(252)
```

-continued

```
<400> SEQUENCE: 2

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
            35                  40                  45

Lys Glu Glu Val Ile Lys Ala Gly Gly Glu Ala Val Val Val Gln Gly
        50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
            115                 120                 125

Lys Tyr Phe Val Glu Asn Asp Ile Lys Gly Asn Val Ile Asn Met Ser
        130                 135                 140

Ser Val His Glu Val Ile Pro Trp Pro Leu Phe Val His Tyr Ala Ala
145                 150                 155                 160

Ser Lys Gly Gly Ile Lys Leu Met Thr Lys Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Lys Ala Asp
            195                 200                 205

Val Glu Ser Met Ile Pro Met Gly Tyr Ile Gly Glu Pro Glu Glu Ile
        210                 215                 220

Ala Ala Val Ala Val Trp Leu Ala Ser Lys Glu Ser Ser Tyr Val Thr
225                 230                 235                 240

Gly Ile Thr Leu Phe Ala Asp Gly Gly Met Thr Leu Tyr Pro Ser Phe
                245                 250                 255

Gln Ala Gly Arg Gly
            260
```